(12) United States Patent
Wolf et al.

(10) Patent No.: US 11,259,722 B2
(45) Date of Patent: Mar. 1, 2022

(54) APPARATUS AND METHOD FOR MEASURING THE BLOOD OXYGEN SATURATION IN A SUBJECT'S TISSUE

(71) Applicants: Carag AG, Baar (CH); Universität Zürich, Zürich (CH)

(72) Inventors: Martin Wolf, Zürich (CH); Helene Isler, Zürich (CH); Daniel Schenk, Affoltern am Albis (CH)

(73) Assignees: Carag AG, Baar (CH); Universität Zürich, Zürich (CH)

( * ) Notice: Subject to any disclaimer, the term of this patent is extended or adjusted under 35 U.S.C. 154(b) by 311 days.

(21) Appl. No.: 16/484,911

(22) PCT Filed: Feb. 9, 2018

(86) PCT No.: PCT/EP2018/053306
§ 371 (c)(1),
(2) Date: Aug. 9, 2019

(87) PCT Pub. No.: WO2018/146261
PCT Pub. Date: Aug. 16, 2018

(65) Prior Publication Data
US 2019/0380633 A1    Dec. 19, 2019

(30) Foreign Application Priority Data

Feb. 10, 2017  (EP) .................................. 17000216

(51) Int. Cl.
  *A61B 5/1455*    (2006.01)
  *A61B 5/1464*    (2006.01)
  *A61B 5/00*      (2006.01)

(52) U.S. Cl.
  CPC ........ *A61B 5/14551* (2013.01); *A61B 5/1464* (2013.01); *A61B 5/7235* (2013.01); *A61B 2503/045* (2013.01)

(58) Field of Classification Search
CPC . A61B 5/1455; A61B 5/14551; A61B 5/1464; A61B 5/7235; A61B 5/7271
See application file for complete search history.

(56) References Cited

U.S. PATENT DOCUMENTS

| 2006/0122475 | A1 | 6/2006 | Balberg et al. |
| 2011/0028812 | A1 | 2/2011 | Benni |
| 2012/0136225 | A1 | 5/2012 | Benni et al. |
| 2013/0281803 | A1 | 10/2013 | Scheele et al. |

FOREIGN PATENT DOCUMENTS

| EP | 1259791 B1 | 11/2013 |
| JP | 2000-193585 A | 7/2000 |

OTHER PUBLICATIONS

English Translation of Japanese Office Action; Application No. 2019-542189, dated Oct. 13, 2020.
Japanese Office Action; Application No. 2019-542189, dated Oct. 13, 2020.
Phong Phan et al; "Multi-Channel Multi-Distance Broadband Near-Infrared Spectroscopy System to Measure the Spatial Response of Cellular Oxygen Metabolism and Tissue Oxygenation"; Biomedical Optics Express 4424; vol. 7, No. 11 Nov. 1, 2016.
Christiana Kolyva et al.: "Cytochrome Coidase Response to Changes in Cerebral Oxygen Delivery in the Adult Brain Shows Higher Brain-Specificity Than Haemoglobin"; vol. 85, May 23, 2013, pp. 234-244.
Euopean Serach Reprot; EP 17 00 0216, dated Aug. 9, 2017.
International Search Report, PCT/EP2018/053306, dated Apr. 30, 2018.

*Primary Examiner* — Eric F Winakur
(74) *Attorney, Agent, or Firm* — Fishman Stewart PLLC

(57) ABSTRACT

An apparatus and method for non-invasively determining the blood oxygen saturation within a subject's tissue by near-infrared spectroscopy is disclosed. Embodiments of the apparatus and method use the multi-distance method and take into account the attenuation of the light signal due to light absorbers other than hemoglobin and deoxyhemoglobin and the scattering properties of a subject's tissue.

13 Claims, No Drawings

APPARATUS AND METHOD FOR MEASURING THE BLOOD OXYGEN SATURATION IN A SUBJECT'S TISSUE

CROSS-REFERENCE TO RELATED APPLICATIONS

This application is a National Stage Patent Application of International Patent Application No. PCT/EP2018/053306, filed Feb. 9, 2018, which claims the benefit of European Application Serial No. 17000216.6, filed Feb. 10, 2017, the contents of each are incorporated by reference in their entireties.

TECHNICAL FIELD

The present invention relates to an apparatus for measuring the blood oxygen saturation in a subject's tissue and to a method for determining the blood oxygen saturation in a subject's tissue.

BACKGROUND

Monitoring blood oxygen saturation in a subject's tissue is of clinical importance, since low blood oxygen saturation is indicative of potentially lethal disorders. This is, for example, the case for preterm infants, which often suffer from impairments of the gestational tract such as necrotizing enterocolitis or obstipation, and are at a constant risk of developing shock. In the case of preterm infants, there is, therefore, the need to constantly and accurately monitor the abdominal oxygen saturation.

The blood oxygen saturation in a subject's tissue is defined as:

$$StO_2 = \frac{c_{HbO_2}}{c_{HbO_2} + c_{Hb}}$$

where $c(HbO_2)$ and $c(Hb)$ are the concentrations of oxy-hemoglobin and deoxyhemoglobin, respectively.

Near-infrared spectroscopy (NIRS) is a non-invasive technique to measure blood oxygen saturation in a subject's tissue. NIRS relies on the distinct absorption characteristics of oxyhemoglobin ($HbO_2$) and deoxyhemoglobin (Hb) in the near-infrared spectral range in order to determine the relative concentrations of $HbO_2$ and Hb. NIRS can be performed non-invasively by placing a spectroscopic sensor on a subject's skin and measuring the attenuation of a light signal after it has passed through the subject's tissue.

The measured light attenuation is related to the concentration of a given light absorbing species (chromophore) by the Lambert-Beer law:

$$A_\lambda = -\log\frac{I_\lambda}{I_{\lambda 0}} = \varepsilon_\lambda c d$$

where $A_\lambda$ is the light attenuation at a particular wavelength $\lambda$, c is the concentration of a particular chromophore, $\varepsilon_\lambda$ is the extinction coefficient of a particular chromophore at a particular wavelength, and d the light source to detector separation distance. Using the known extinction coefficient, a chromophore's concentration can be calculated from the measured light attenuation. In the case of a mixture of different chromophores, the relative concentrations of the chromophores can be determined by measuring light attenuation at several distinct wavelengths, at which the extinction coefficients of the chromophores differ. For a mixture comprising N different chromophores, this requires measuring the attenuation at a minimum of N different wavelengths.

In a typical NIRS apparatus, a light signal of a known wavelength and intensity is transmitted into a subject's tissue and the light that is diffusely reflected from the tissue is detected to calculate the light attenuation. To accurately determine the concentration of chromophores in a tissue form the measured light attenuation, it is necessary to account for the optical properties of the tissue, in particular absorption due to other chromophores present in the tissue and the tissue's scattering properties. In practice, the tissue's scattering properties need to be accounted for by calibration measurements. To account for chromophores other than $HbO_2$ and Hb, the absorption spectra of these chromophores have to be determined in order to estimate the wavelength-dependent extinction coefficients, and the light attenuation has to be measured at a minimum of 2+M wavelengths, where M is the number of additional chromophores that should be accounted for. Several methods for addressing these problems have been developed in the prior art.

EP 1 259 791 B1 discloses a NIRS method for measuring the total blood oxygen saturation within a subject's tissue by measuring the light attenuation at three or more wavelengths and calculating the difference in attenuation between the wavelengths. This approach is also known as the "differential wavelength method". This method requires measuring at N+1 different wavelengths in order to determine the concentrations of N different chromophores. By determining the differential attenuation, the contributions of tissue light scattering, fixed light absorbing components, and measuring apparatus characteristics are minimized relative to the attenuation attributable to $HbO_2$ and Hb, which improves the accuracy of the measured blood oxygen saturation.

US 2012/0136225 A1 discloses a method for determining the blood oxygen saturation within a subject's lower gastro-intestinal tissue that involves taking into account the presence of wavelength dependent absorbing material not present in blood. Specifically, US 2012/0136225 A1 suggests taking into account light attenuation due to stool present in a subject's lower gastro-intestinal tract, particularly meconium present in the gastro-intestinal tract of new-born infants. US 2012/0136225 A1 also teaches the use of the differential wavelength method for analyzing NIRS data.

Although the differential wavelength method minimizes the contribution of the scattering properties of the tissue, it still requires calibration to account for scattering as well as unspecific background absorption. This calibration is performed by determining the blood oxygen saturation of a given reference tissue assuming that the oxygen saturation of said reference tissue is the weighted sum of the oxygen saturation of a subject's venous and arterial blood. This, however, requires knowledge of the relative contributions of venous and arterial blood in that tissue. Although empirical data for the relative contributions of venous and arterial blood oxygen saturation exist, the reliability of this data is questionable. Thus, the available calibration methods present a potential source of error for the differential wavelength method.

An alternative method for performing NIRS measurements is to measure light attenuation at several wavelengths and at several different distances between the light source and the light detectors. The absorption $\mu_{a,\lambda}$ at a particular wavelength $\lambda$ can then be calculated based on the following equation:

$$\mu_{a,\lambda} = \frac{1}{3\mu_{s,\lambda}} \left( \ln 10 \frac{\partial A}{\partial d} - \frac{1}{d} \right)^2$$

where $\mu_{s,\lambda}$ is an empirically determined value that accounts for attenuation of the light signal due to light scattering in the subject's tissue at the particular wavelength $\lambda$, $A_\lambda$ is the attenuation at the particular wavelength $\lambda$, d is the mean distance between light source and detectors, and $\partial A_\lambda/\partial d$ is the slope of the attenuation versus the light source to detector distance. The concentration of chromophores can be calculated from the absorption $\mu_{a,\lambda}$ using the Lambert-Beer law. This approach is also known as the "multi-distance method". It has been applied to measure the blood oxygen saturation of muscle tissue (Tachtsidis, Ilias et al. "A Hybrid Multi-Distance Phase and Broadband Spatially Resolved Spectrometer and Algorithm for Resolving Absolute Concentrations of Chromophores in the Near-Infrared Light Spectrum." Advances in Experimental Medicine and Biology 662 (2010): 169-175). However, the reported approach does not take into account other absorbers than $HbO_2$ and Hb, in particular light absorbers present in a subject's abdomen.

SUMMARY

Thus, it is an object of the present invention to provide an NIRS apparatus and method for more accurately determining the blood oxygen saturation in a subject's tissue. The invention particularly aims at more accurately measuring the blood oxygen saturation in the abdomen of new-born infants, in particular preterm infants.

To solve this problem, the invention has found that blood oxygen saturation within a subject's tissue can be more accurately determined using a multi-distance method and accounting for the absorption due to light absorbers other than hemoglobin and deoxyhemoglobin in a subject's tissue as well as due to light scattering in a subject's tissue.

The invention, therefore, relates to an apparatus for non-invasively determining the blood oxygen saturation within a subject's tissue, comprising at least one light source for transmitting a light signal into the subject's tissue;

at least one light detector for detecting the light signal from the light sources after it has passed through the subject's tissue, wherein the one or more light sources and the one or more light detectors are configured to measure the attenuation of the light signal at two or more light source to detector distances; and a processor connected to the light sources and the light detectors, characterized in that the one or more light sources and the one or more light detectors are configured to measure the attenuation of the light signal at three or more distinct wavelengths in the range of 650 nm to 3 µm, and the processor includes an algorithm for determining the attenuation of the light signal as a function of the wavelength and the light source to detector distance;

calculating the slope of the attenuation of the light signal versus the light source to detector distance as a function of the wavelength; and calculating the blood oxygen saturation within the subject's tissue on the basis of said slope of the attenuation of the light signal and empirically determined data that account for attenuation of the light signal due to light absorbers other than hemoglobin and deoxyhemoglobin in the subject's tissue and due to light scattering in the subject's tissue.

By measuring the attenuation as a function of the light source to detector distance, it is possible to calculate the relative absorption using the multi-distance approach. This removes the necessity of performing calibration by determining the blood oxygen saturation of a given reference tissue assuming that oxygen saturation of said reference tissue is the weighted sum of the oxygen saturation of a subject's venous and arterial blood. The invention only needs to account for light scattering of the tissue. This removes a source of systematic error, since it no longer requires any assumptions on the relative contributions of venous and arterial blood.

By measuring light attenuation at three or more distinct wavelengths and using empirically determined data accounting for attenuation of the light signal due to light absorbers other than hemoglobin and deoxyhemoglobin, it is possible to account for attenuation due to, for example, stool or other absorbers present in the subject's tissue. This is of particular importance when measuring the blood oxygen saturation in the abdomen of new-born infants, where stool has a significant influence on the absorption properties in the near-infrared range. The data can be easily determined using samples of known absorbers, for example stool samples taken from a number of new-born infants. This significantly improves the accuracy of the measured blood oxygen saturation.

The light sources and the light detectors are configured to transmit the light signal into a subject's tissue and to detect the light signal after it has passed through the subject's tissue. Preferably, the light sources and the light detectors are configured such that the detectors detect the light that is diffusely reflected from within the subject's tissue. Preferably, the light sources and the light detectors are configured such that they can be brought into direct contact with the subject's skin in order to avoid any interference with ambient light.

The light sources may be broadband light sources emitting light over a range of wavelengths. Alternatively, the light sources may be a collection of light sources each emitting light at a narrow spectral bandwidth, such as a collection of light emitting diodes. In a preferred embodiment, the light sources include a collection of light emitting diodes each emitting light at a different wavelength.

The light detectors may be, for example, photodiodes or any other device that can convert light to an electrical current. Each detector may comprise a collection of individual detectors, each of which detects light at a different wavelength.

The light sources and the light detectors are configured to measure the attenuation of the light signal at two or more light source to detector distances. This enables the apparatus to determine the attenuation of the light signal as a function of the light source to detector distance and to perform an analysis according to the multi-distance method.

DETAILED DESCRIPTION

In one embodiment, the apparatus comprises a single light source and two or more light detectors positioned at fixed distances from the light source. Alternatively, the apparatus comprises a single light detector and two or more light sources positioned at fixed distances from the light detector. In these embodiments, the light source to detector distances do not change during the measurement.

In yet another embodiment, the apparatus comprises a single light source and a single light detector, wherein the light source and/or the light detector are movable in order to vary the light source to detector distance during the measurement. This embodiment has the advantage that the attenuation of the light signal as a function of the light source to detector distance can be sampled over a wide range and a large number of data points.

The light sources and the light detectors are configured to measure of the attenuation of the light signal at three or more distinct wavelengths in the range of 650 nm to 3 μm, preferably in the range of 650 nm to 1 μm, more preferably in the range of 680 nm to 950 nm. For example, each light source may be a collection of individual light sources each emitting light at a narrow spectral bandwidth. In this case, the detectors may be broadband detectors that can detect light at least at these spectral ranges. Alternatively, the light sources may be broadband light sources and a diffraction grating or specific emission filters may be used to detect the light in a wavelength-specific manner.

In order to increase the accuracy of the measurement, attenuation is preferably measured at four or more distinct wavelengths, more preferably at five or more, most preferably at seven or more. In a particularly preferred embodiment the light detectors are configured to measure of the attenuation of the light signal at seven distinct wavelengths in the range of 650 nm to 1 μm.

In the case of performing the measurement on a subject's abdomen, in particular the abdomen of a new-born infant, it has been found that measuring in the range of 815 to 875 nm does not increase the accuracy of the measurement. Therefore, the light detectors are configured to measure of the attenuation of the light signal at seven distinct wavelengths in the range of 650 nm to 1 μm, excluding the range of 815 to 875 nm.

In the case of performing the measurement on a subject's abdomen, several combinations of wavelengths have been found that offer an increased measurement accuracy. These wavelengths can be selected to better distinguish between Hb, $HbO_2$, and other absorbers present in a subject's abdomen, such as stool. These optimized combinations of wavelengths are set out in the following.

In one embodiment, the light detectors are configured to measure of the attenuation of the at three or more distinct wavelengths selected from 695±5 nm, 712±5 nm, 733±5 nm, 743±5 nm, 762±5 nm, 783±5 nm, 790±5 nm, 805±5 nm, 880±5 nm, 895±5 nm, and 910±5 nm. Preferably, the wavelengths are selected from 712±5 nm, 733±5 nm, 762±5 nm, 783±5 nm, 805±5 nm, 880±5 nm, 895±5 nm, and 910±5 nm.

In one embodiment, the light detectors are configured to measure of the attenuation of the light signal at 712±5 nm, 736±5 nm, 762±5 nm, 784±5 nm, and 910±5 nm.

In one embodiment, the light detectors are configured to measure of the attenuation of the light signal at 712±5 nm, 736±5 nm, 762±5 nm, 784±5 nm, 895±5 nm, and 910±5 nm.

In order to measure the attenuation at a given number of distinct wavelengths, it is sufficient that the light sources and the light detectors are configured to measure the attenuation at distinct wavelength ranges, which at least include the specified wavelength. The spectral bandwidth of each wavelength range may vary, as long as the wavelength ranges can be clearly distinguished. Preferably, the attenuation is measured at distinct wavelength ranges having a bandwidth of ±25 nm or less, more preferably ±15 nm or less, most preferably ±5 nm or less.

In a preferred embodiment, the apparatus is configured to measure the attenuation at more than two light source to detector distances in order to improve the accuracy of the calculated slope of the attenuation of the light signal versus the light source to detector distance as a function of the wavelength. In a preferred embodiment, the apparatus is configured to measure the attenuation at three light source to detector distances.

The minimum and maximum light source to detector distances can be optimized based on the sensitivity of the detectors and the optical properties of the subject's tissue. In the case of an apparatus for measuring the blood oxygen saturation in the abdomen of a new-born infant, the minimum light source to detector distance is preferably at least 0.8 cm, more preferably at least 0.9 cm, and most preferably at least 1.0 cm. Preferably, the shortest distance between the light source and the detectors is in the range of 0.8 to 2 cm, more preferably at least 0.9 to 1.5 cm, and most preferably 0.95 to 1.2 cm. The longest light source to detector distance is preferably in the range of 2 to 10 cm, preferably 3 to 8 cm, most preferably 4 to 6 cm.

The algorithm calculates the blood oxygen saturation within the subject's tissue on the basis of the slope of the attenuation of the light signal versus the light source to detector distance as a function of the wavelength. Thus, the algorithm calculates the blood oxygen saturation level using the multi-distance method.

In a preferred embodiment, the algorithm included in the processor calculates the relative absorption $\mu_{a,\lambda}$ at a particular wavelength $\lambda$ based on the following equation:

$$\mu_{a,\lambda} = \frac{1}{3\mu_{s,\lambda}}\left(\ln 10 \frac{\partial A}{\partial d} - \frac{1}{d}\right)^2$$

where $\mu_{s,\lambda}$ is an empirically determined value that accounts for attenuation of the light signal due to light scattering in the subject's tissue at the particular wavelength $\lambda$, $A_\lambda$ is the attenuation at the particular wavelength $\lambda$, d is the mean light source to detector distance, and $\partial A_\lambda/\partial d$ is the slope of the attenuation versus the light source to detector distance.

It should be noted that the above formula calculates the relative absorption $\mu_{a,\lambda}$, which is equal to the absolute absorption multiplied with a factor k. This factor can be determined using calibration measurements. Using the relative absorption, is sufficient to calculate the relative concentrations of chromophores. Since the blood oxygen saturation as defined above is the ratio of the $HbO_2$ concentration to the total hemoglobin concentration, it is not necessary to determine the absolute concentration of $HbO_2$ and Hb. therefore, it is not necessary to determine the factor k, and k has been omitted from the above formula for $\mu_{a,\lambda}$.

The absorption $\mu_{a,\lambda}$ can then be used to calculate the concentrations of $HbO_2$, Hb and other light absorbers using the Lambert-Beer law.

The reduced scattering $\mu_{s,\lambda}$ is an empirically determined value that accounts for attenuation of the light signal due to light scattering in the subject's tissue. To calculate the relative absorption $\mu_{a,\lambda}$ according to above-mentioned formula, it is sufficient to know the relative reduced scattering $\mu_{s,\lambda}$, which is defined as $$\mu_{s,\lambda} = (1 - h\lambda)$$

where h is a scattering parameter of a particular tissue. The scattering parameter h can be determined from measuring the scattering properties of reference tissue. For example, h is determined by measuring the scattering properties of the abdomen of a number of new-born infants. In a preferred embodiment, the parameter h is assumed to be in the range of 10-4 to 10-3 nm-1, preferably 2·10-4 to 8·10-4 nm-1, more preferably 5·10-4 to 8·10-4 nm-1. In a particularly preferred embodiment, h is assumed to be 6.4·10-4 nm-1. It has been found that these values accurately account for scattering in the abdomen of a new-born infant.

The absolute reduced scattering can be determined by multiplying $\mu_{s,\lambda}$ as defined above with a factor k. For the present invention, however, it is not necessary to determine k.

The parameters h and k can be experimentally determined by frequency domain absorption measurements as described, for example, in Sergio Fantini, Maria Angela Franceschini, Joshua B. Fishkin, Beniamino Barbieri, and Enrico Gratton, "Quantitative determination of the absorption spectra of chromophores in strongly scattering media: a light-emitting-diode based technique," Appl. Opt. 33, 5204-5213 (1994).

In one embodiment, the algorithm calculates the blood oxygen saturation by calculating the relative concentrations of $HbO_2$ and Hb according to the following equation:

$$\begin{pmatrix} c_{Hb} \\ c_{HbO_2} \\ c_{other} \end{pmatrix} = \begin{pmatrix} \varepsilon_{Hb,\lambda_1} & \varepsilon_{HbO_2,\lambda_1} & \varepsilon_{other,\lambda_1} \\ \varepsilon_{Hb,\lambda_2} & \varepsilon_{HbO_2,\lambda_2} & \varepsilon_{other,\lambda_2} \\ \varepsilon_{Hb,\lambda_3} & \varepsilon_{HbO_2,\lambda_3} & \varepsilon_{other,\lambda_3} \end{pmatrix}^{-1} \begin{pmatrix} \mu_{a,\lambda_1} \\ \mu_{a,\lambda_2} \\ \mu_{a,\lambda_3} \end{pmatrix}$$

where $c_{HbO2}$ and $c_{Hb}$ are the relative concentrations of oxyhemoglobin and deoxyhemoglobin, respectively, $\mu_{a,\lambda n}$ is the absorption determined at the particular wavelength $\lambda n$ according to the equation given above, $c_{other}$ is the concentration of light absorbers other than hemoglobin and deoxyhemoglobin present in the subject's tissue, and $\varepsilon_{x,\lambda n}$ is the extinction coefficient for the light absorbing species x at the particular wavelength $\lambda n$.

The relative concentrations calculated according to this formula are equal to the absolute concentrations multiplied by a factor k. However, to calculate the blood oxygen saturation $StO_2$ it is sufficient to use the relative concentrations and the following equation:

$$StO_2 = \frac{c_{HbO_2}}{c_{HbO_2} + c_{Hb}}$$

The values for $\varepsilon_{x,\lambda n}$ represent data accounting for attenuation of the light signal due to light absorbers. These data can be determined empirically by measuring the absorption spectra of the respective light absorbers in isolation.

In order to improve the accuracy when measuring the blood oxygen saturation of new-born infants, it is necessary to account for absorption due to meconium and transitional stool.

In one particular embodiment, $\varepsilon_{other,\lambda n}$ is determined by measuring the absorption spectra of isolated samples of stool, transitional stool, meconium, and/or biliverdin. In a preferred example, $\varepsilon_{other,\lambda n}$ is determined by measuring the absorption spectra of isolated samples of meconium.

Meconium is the earliest stool of a mammalian infant. Meconium is composed of materials ingested during the time the infant spends in the uterus: intestinal epithelial cells, lanugo, mucus, amniotic fluid, bile, and water. It has been found that averaged absorption spectra of meconium samples taken from number of different subjects can be used as a source of extinction data for the above calculation. In one embodiment, the data accounting for attenuation of the light signal due to light absorbers therefore include the wavelength-dependent extinction coefficients of meconium samples taken from new-born infants.

Transitional stool is produced by a new-born infant during its first days of life. Transitional stool differs from meconium in its composition and comprises high amounts of biliverdin. Therefore, the data accounting for attenuation of the light signal due to light absorbers preferably include the wavelength-dependent extinction coefficients of transitional stool samples taken from new-born infants, preferably during the first two weeks after birth, more preferably during the first week after birth, most preferably during the first five days after birth.

In another preferred embodiment, the data accounting for attenuation of the light signal due to light absorbers therefore include the wavelength-dependent extinction coefficients of biliverdin.

In another aspect, the present invention also provides a method for non-invasively determining the blood oxygen saturation within a subject's tissue, comprising the steps of transmitting a light signal from at least one light source into the subject's tissue; and detecting the light signal after it has passed through the subject's tissue at one or more detection points and at least two different light source to detector distances; characterized in that the method further comprises the steps of measuring the attenuation of the light signal at three or more distinct wavelengths in the range of 650 nm to 3 μm, determining the attenuation of the light signal as a function of the wavelength and the light source to detector distance;

calculating the slope of the attenuation of the light signal versus the light source to detector distance as a function of the wavelength; and calculating the blood oxygen saturation within the subject's tissue on the basis of said slope of the attenuation of the light signal and empirically determined data that account for attenuation of the light signal due to light absorbers other than hemoglobin and deoxyhemoglobin in the subject's tissue and due to light scattering in the subject's tissue.

This method is particularly suited to determine blood oxygen saturation in the abdomen of new-born infants, as it allows to account for the presence of light absorbing species, such as meconium and transitional stool, and can provide accurate measurements of the blood oxygen saturation. In a preferred embodiment, the method is therefore carried out on the subject's abdomen. The subject preferably is an infant. Preferably, the infant is at most one year old, more preferably at most six months old, most preferably at most three months old. The method is particularly useful for non-invasively measuring the blood oxygen saturation of preterm infants.

The light source to detector distance is preferably set as discussed above for the apparatus of the invention.

Preferably, the attenuation of the light signal is measured at three or more distinct wavelengths selected from 695±5 nm, 712±5 nm, 733±5 nm, 743±5 nm, 762±5 nm, 783±5 nm, 790±5 nm, 805±5 nm, 880±5 nm, 895±5 nm, and 910±5 nm. Preferably, the wavelengths are selected from 712±5 nm, 733±5 nm, 762±5 nm, 783±5 nm, 805±5 nm, 880±5 nm, 895±5 nm, and 910±5 nm.

In one embodiment, the attenuation of the light signal is measured at 712±5 nm, 736±5 nm, 762±5 nm, 784±5 nm, and 910±5 nm.

In one embodiment, the attenuation of the light signal is measured at 712±5 nm, 736±5 nm, 762±5 nm, 784±5 nm, 895±5 nm, and 910±5 nm.

The step of calculating the blood oxygen saturation preferably involves the same steps as discussed above for the algorithm of the inventive apparatus.

Preferably, the step of calculating the blood oxygen saturation within the subject's tissue involves calculating the relative absorption $\lambda_{a,\lambda}$ at a particular wavelength $\lambda$ based on the following equation:

$$\mu_{a,\lambda} = \frac{1}{3\mu_{s,\lambda}}\left(\ln 10 \frac{\partial A}{\partial d} - \frac{1}{d}\right)^2$$

where $\mu_{s,\lambda}$ is an empirically determined value that accounts for attenuation of the light signal due to light scattering in the subject's tissue at the particular wavelength $\lambda$, $A_\lambda$ is the attenuation at the particular wavelength $\lambda$, d is the mean distance between light source and detectors, and $\partial A_\lambda/\partial d$ is the slope of the attenuation versus the light source to detector distance.

Preferably, $\mu_{s,\lambda}$ is $$\mu_{s,\lambda} = (1 - h\lambda)$$

where h is assumed to be in the range of 10-4 to 10-3 nm-1.

Preferably, the step of calculating the blood oxygen saturation includes the step of calculating the relative concentrations of oxyhemoglobin and deoxyhemoglobin in the subject's tissue according to the following equation $$\begin{pmatrix} c_{Hb} \\ c_{HbO_2} \\ c_{other} \end{pmatrix} = \begin{pmatrix} \varepsilon_{Hb,\lambda_1} & \varepsilon_{HbO_2,\lambda_1} & \varepsilon_{other,\lambda_1} \\ \varepsilon_{Hb,\lambda_2} & \varepsilon_{HbO_2,\lambda_2} & \varepsilon_{other,\lambda_2} \\ \varepsilon_{Hb,\lambda_3} & \varepsilon_{HbO_2,\lambda_3} & \varepsilon_{other,\lambda_3} \end{pmatrix}^{-1} \begin{pmatrix} \mu_{a,\lambda_1} \\ \mu_{a,\lambda_2} \\ \mu_{a,\lambda_3} \end{pmatrix}$$

where $C_{HbO2}$ and $c_{Hb}$ are the relative concentrations of oxyhemoglobin and deoxyhemoglobin, respectively, $\mu_{a,\lambda n}$ is the absorption determined at the particular wavelength $\lambda n$ according to the equation given above, $c_{other}$ is the concentration of light absorbers other than hemoglobin and deoxyhemoglobin present in the subject's tissue, and $\varepsilon_{x,\lambda n}$ is the extinction coefficient for the light absorbing species x at the particular wavelength $\lambda n$.

Preferably, the blood oxygen saturation St0$_2$ is calculated from the relative concentrations of HbO$_2$ and Hb according to the following equation:

$$StO_2 = \frac{c_{HbO_2}}{c_{HbO_2} + c_{Hb}}$$

Preferably, the data accounting for attenuation of the light signal due to light absorbers include the data accounting for attenuation of the light signal due to light absorbers include the wavelength-dependent extinction coefficients one or more of meconium samples taken from new-born infants, transitional stool samples taken from new-born infants, and biliverdin.

The invention claimed is:

1. An apparatus for non-invasively determining blood oxygen saturation within a subject's tissue, comprising:
   at least one light source for transmitting a light signal into the subject's tissue;
   at least one light detector for detecting the light signal from the at least one light source after it has passed through the subject's tissue, wherein the at least one light source and the at least one light detector are configured to measure an attenuation of the light signal at two or more light source to detector distances; and
   a processor connected to the light sources and the light detectors, and wherein, at least one light source and the at least one light detector are configured to measure the attenuation of the light signal at three or more distinct wavelengths in a range of 650 nm to 3 μm, and the processor includes an algorithm for:
   determining the attenuation of the light signal as a function of wavelength and light source to detector distance;
   calculating a slope of the attenuation of the light signal versus the light source to detector distance as a function of the wavelength; and
   calculating a blood oxygen saturation within the subject's tissue on the basis of said slope of the attenuation of the light signal and empirically determined data that account for attenuation of the light signal due to light absorbers other than hemoglobin and deoxyhemoglobin in the subject's tissue and due to light scattering in the subject's tissue;
   wherein the data accounting for attenuation of the light signal due to light absorbers include the wavelength-dependent extinction coefficients of one or more of meconium samples taken from new-born infants, transitional stool samples taken from new-born infants, and biliverdin.

2. The apparatus of claim 1, wherein the light source and the detectors are configured to measure the attenuation of the light signal at three or more distinct wavelengths selected from 695±5 nm, 712±5 nm, 733±5 nm, 743±5 nm, 762±5 nm, 783±5 nm, 790±5 nm, 805±5 nm, 880±5 nm, 895±5 nm, and 910±5 nm.

3. The apparatus of claim 1, wherein the minimum light source to detector distance is at least 0.8 cm.

4. The apparatus of claim 1, wherein the algorithm includes the step of calculating a relative absorption $\mu_{a,\lambda}$ at a particular wavelength $\lambda$ based on the following equation:

$$\mu_{a,\lambda} = \frac{1}{3\mu_{s,\lambda}}\left(\ln 10 \frac{\partial A}{\partial d} - \frac{1}{d}\right)^2$$

where $\mu_{s,\lambda}$ is an empirically determined value that accounts for attenuation of the light signal due to light scattering in the subject's tissue at the particular wavelength $\lambda$, $A_\lambda$ is the attenuation at the particular wavelength $\lambda$, d is the mean light source to detector distance, and $\partial A_\lambda/\partial d$ is the slope of the attenuation versus the light source to detector distance.

5. The apparatus of claim 4, wherein $\mu_{s,\lambda}$ is $$\mu_{s,\lambda} = (1 - h\lambda)$$

where h is assumed to be in the range of $10^{-4}$ to $10^{-3}$ nm$^{-1}$.

6. The apparatus of claim 4, wherein the algorithm includes the step of calculating the relative concentrations of oxyhemoglobin and deoxyhemoglobin in the subject's tissue according to the following equation $$\begin{pmatrix} c_{Hb} \\ c_{HbO_2} \\ c_{other} \end{pmatrix} = \begin{pmatrix} \varepsilon_{Hb,\lambda_1} & \varepsilon_{HbO_2,\lambda_1} & \varepsilon_{other,\lambda_1} \\ \varepsilon_{Hb,\lambda_2} & \varepsilon_{HbO_2,\lambda_2} & \varepsilon_{other,\lambda_2} \\ \varepsilon_{Hb,\lambda_3} & \varepsilon_{HbO_2,\lambda_3} & \varepsilon_{other,\lambda_3} \end{pmatrix}^{-1} \begin{pmatrix} \mu_{a,\lambda_1} \\ \mu_{a,\lambda_2} \\ \mu_{a,\lambda_3} \end{pmatrix}$$

where $C_{HbO2}$ and $c_{Hb}$ are the relative concentrations of oxyhemoglobin and deoxyhemoglobin, respectively, $\mu_{a,\lambda n}$ is the absorption determined at the particular wavelength $\lambda n$ according to the equation given above, $c_{other}$ is the concentration of light absorbers other than hemoglobin and deoxyhemoglobin present in the subject's tissue, and $\varepsilon_{x,\lambda n}$ is the extinction coefficient for the light absorbing species x at the particular wavelength $\lambda n$.

7. A method for non-invasively determining the blood oxygen saturation within a subject's tissue, comprising:
   transmitting a light signal from at least one light source into the subject's tissue; and
   detecting the light signal after it has passed through the subject's tissue at one or more detection points and at least two different light sources to detector distances;
   wherein the method further includes: measuring the attenuation of the light signal at three or more distinct wavelengths in the range of 650 nm to 3 μm, determining the attenuation of the light signal as a function of the wavelength and the light source to detector distance;
   calculating the slope of the attenuation of the light signal versus the light source to detector distance as a function of the wavelength; and
   calculating the blood oxygen saturation within the subject's tissue on the basis of said slope of the attenuation of the light signal and empirically determined data that account for attenuation of the light signal due to light absorbers other than hemoglobin and deoxyhemoglobin in the subject's tissue and due to light scattering in the subject's tissue;
   wherein the data accounting for attenuation of the light signal due to light absorbers include the wavelength-dependent extinction coefficients one or more of meconium samples taken from new-born infants, transitional stool samples taken from new-born infants, and biliverdin.

8. The method of claim 7, wherein the subject's tissue is the subject's abdomen.

9. The method of claim 7, wherein the subject is an at most a one year old infant.

10. The method of claim 7, wherein the minimum light source to detector distance is set to at least 0.8 cm.

11. The method of claim 7, wherein the step of calculating the blood oxygen saturation within the subject's tissue involves calculating the relative absorption $\mu_{a,\lambda}$ at a particular wavelength $\lambda$ based on the following equation:

$$\mu_{a,\lambda} = \frac{1}{3\mu_{s,\lambda}}\left(\ln 10 \frac{\partial A}{\partial d} - \frac{1}{d}\right)^2$$

where $\mu_{s,\lambda}$ is an empirically determined value that accounts for attenuation of the light signal due to light scattering in the subject's tissue at the particular wavelength $\lambda$, $A_\lambda$ is the attenuation at the particular wavelength $\lambda$, d is the mean distance between light source and detectors, and $\partial A_\lambda/\partial d$ is the slope of the attenuation versus the light source to detector distance.

12. The method of claim 11,
wherein $\mu_{s,\lambda}$ is $$\mu_{s,\lambda} = (1 - h\lambda)$$

where h is assumed to be in the range of $10^{-4}$ to $10^{-3}$ nm$^{-4}$.

13. The method of claim 11,
where the step of calculating the blood oxygen saturation within the subject's tissue includes the step of calculating the relative concentrations of oxyhemoglobin and deoxyhemoglobin in the subject's tissue according to the following equation $$\begin{pmatrix} c_{Hb} \\ c_{HbO_2} \\ c_{other} \end{pmatrix} = \begin{pmatrix} \varepsilon_{Hb,\lambda_1} & \varepsilon_{HbO_2,\lambda_1} & \varepsilon_{other,\lambda_1} \\ \varepsilon_{Hb,\lambda_2} & \varepsilon_{HbO_2,\lambda_2} & \varepsilon_{other,\lambda_2} \\ \varepsilon_{Hb,\lambda_3} & \varepsilon_{HbO_2,\lambda_3} & \varepsilon_{other,\lambda_3} \end{pmatrix}^{-1} \begin{pmatrix} \mu_{a,\lambda_1} \\ \mu_{a,\lambda_2} \\ \mu_{a,\lambda_3} \end{pmatrix}$$

where $C_{HbO2}$ and $c_{Hb}$ are the relative concentrations of oxyhemoglobin and deoxyhemoglobin, respectively, $\mu_{a,\lambda n}$ is the absorption determined at the particular wavelength $\lambda n$ according to the equation given above, $c_{other}$ is the concentration of light absorbers other than hemoglobin and deoxyhemoglobin present in the subject's tissue, and $\varepsilon_{x,\lambda n}$ is the extinction coefficient for the light absorbing species x at the particular wavelength $\lambda n$.

* * * * *